United States Patent [19]

White

[11] 4,264,775

[45] Apr. 28, 1981

[54] SYNTHESIS OF β-AMINOSTYRENES

[75] Inventor: William A. White, Fountaintown, Ind.

[73] Assignee: Eli Lilly and Company, Indianapolis, Ind.

[21] Appl. No.: 736,008

[22] Filed: Oct. 27, 1976

[51] Int. Cl.$^3$ ............................................. C07C 87/28
[52] U.S. Cl. ............................. 564/383; 260/326.47; 260/326.62; 260/326.87; 260/465 E; 544/162; 544/163; 546/192; 546/329; 546/330; 560/103; 560/105; 560/231; 560/106; 560/111; 564/374
[58] Field of Search .......... 260/570.8 R, 247, 247.2 R, 260/293.72, 293.75, 326.87, 465 D, 326.47, 326.62, 240; 544/162, 163

[56] References Cited

U.S. PATENT DOCUMENTS

| | | | |
|---|---|---|---|
| 3,331,875 | 7/1967 | Strickland | 260/570.8 X |
| 3,454,565 | 7/1969 | Safir et al. | 260/570.8 X |

OTHER PUBLICATIONS

Adams et al., "Organic Reactions," vol. 11, pp. 192, 204, 206–210, 214–215 and 232–234, (1960).
Wagner et al., pp. 38–39 and 669 (1953), "Synthetic Organic Chemistry".
Malinowski, "Roczniki Chem.", vol. 29, pp. 37–45 (1955).
Koelsch, "Jour. Amer. Chem. Soc.", vol. 65, pp. 57–58 (1943).
Kochi, "Jour. Amer. Chem. Soc.", vol. 77, pp. 5090–5092 (1955).

*Primary Examiner*—Robert V. Hines
*Attorney, Agent, or Firm*—Leroy Whitaker; Joseph A. Jones; Arthur R. Whale

[57] ABSTRACT

A simple process for the preparation of β-aminostyrenes proceeds from anilines by successively diazotizing, reacting with a vinyl ester, and reacting with a secondary amine without purification of the intermediate products. The compounds are reactive enamines useful in organic synthesis.

48 Claims, No Drawings

SYNTHESIS OF β-AMINOSTYRENES

BACKGROUND OF THE INVENTION

An important series of 4-pyridone herbicides is disclosed in U.S. patent application No. 591,661, filed July 3, 1975, and in Belgian Pat. No. 832,702. These compounds, which have a phenyl or substituted-phenyl group at the 3-position, are exceptionally potent herbicides particularly for use in cotton cropland.

The present invention belongs to the field of synthetic organic chemistry and agricultural chemistry and provides an economical and convenient process for the preparation of intermediates used in a synthesis of the 4-pyridone herbicides.

SUMMARY OF THE INVENTION

The present invention is a process for preparing a β-aminostyrene of the formula

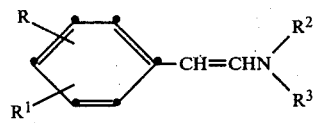

wherein R represents trifluoromethyl, cyano, fluoro, chloro, bromo or nitro;

$R^1$ represents hydrogen, fluoro, chloro, bromo or nitro;

$R^2$ and $R^3$ independently represent $C_1$-$C_3$ alkyl, or $R^2$ and $R^3$ combine with the nitrogen atom to which they are attached to form pyrrolidino, piperidino or morpholino; which process comprises (1) contacting an aniline of the formula

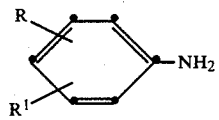

with a nitrite capable of forming diazonium salts, in aqueous hydrochloric acid at a temperature from about $-10°$ to about $10°$ to form the diazonium chloride salt;

(2) contacting said diazonium salt with a vinyl ester of the formula

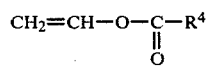

wherein $R^4$ represents $C_1$-$C_3$ alkyl, phenyl, benzyl or hydrogen, in an aqueous, water-miscible alcohol or ketone in the presence of a copper salt and an alkali metal sulfite at a temperature from about 0° to about 40° and a pH from about 4 to about 5 to produce a phenethyl ester of the formula

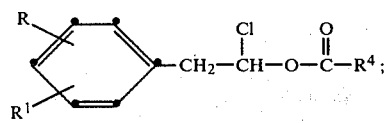

(3) contacting said phenethyl ester with an amine of the formula

at a temperature from about 0° to about 80° in the presence of an acid scavenger to produce the aminostyrene.

DESCRIPTION OF THE PREFERRED EMBODIMENT

Throughout this document, all amounts, ratios, and parts will refer to amounts, ratios, and parts by weight unless otherwise stated. All temperatures are on the Celsius scale.

The term $C_1$-$C_3$ alkyl refers to the groups methyl, ethyl, propyl and isopropyl.

The term alkali metal refers to sodium, potassium and lithium.

A group of typical starting compounds used in the process of this invention will first be shown, to assure that those of organic chemical skill can understand the compounds which are used in the process. The various steps and reaction conditions will then be discussed in detail.

The following compounds are typical anilines used as starting compounds in the process.
  3,5-dichloroaniline
  2-bromoaniline
  2-nitro-5-trifluoromethylaniline
  3-fluoro-4-trifluoromethylaniline
  3-fluoroaniline
  2-chloro-4-nitroaniline
  4-bromo-3chloroaniline
  2,3-difluoroaniline
  2,4-dibromoaniline
  3-cyanoaniline
  3-bromo-4-cyanoaniline
  3,5-dinitroaniline The following compounds are typical vinyl esters used in the process.
  formic acid, vinyl ester
  acetic acid, vinyl ester
  propionic acid, vinyl ester
  2-methylpropionic acid, vinyl ester
  benzoic acid, vinyl ester
  phenylacetic acid, vinyl ester Exemplary amines used in the final step of the process include the following.
  methylethylamine
  methylpropylamine
  diisopropylamine
  ethylpropylamine
  dipropylamine
  morpholine
  pyrrolidine
  piperidine The three steps of the reaction will be discussed separately.

Diazotization Step

In the first step of the process, the aniline is reacted with a nitrite to convert it to the diazonium chloride salt. The nitrite may be any which is capable of forming diazonium salts, of which alkali metal nitrites and in particular sodium nitrite are preferred. Phenyl nitrite and alkyl nitrites, including methyl, ethyl, propyl, and hexyl nitrite may also be used if desired.

The reaction medium for the diazotization step is aqueous hydrochloric acid. The preferred concentration of hydrochloric acid in the reaction medium is about 60–70 percent. The concentration is not critical, however, and hydrochloric acid contents in the range of 40–90 percent may be used. The preferred reaction temperature is about 0°, and the temperature range is from about −10° to about 10°.

Coupling Step

No purification of the diazonium chloride salt prepared in the first step is necessary or advisable. The second, coupling, step is carried out in a medium comprised of a water-miscible alcohol or ketone and water. The preferred solvent is methanol, but other alcohols such as ethanol and isopropanol, and ketones such as acetone, methyl ethyl ketone and the like may also be used.

The coupling step is carried out in the presence of catalytic amounts of a copper salt and an alkali metal sulfite. The preferred copper salt is cupric sulfate, and the preferred sulfite is sodium sulfite. Many copper salts, both cupric and cuprous, may be used, including chlorides, nitrates, bromides, borates, acetates, carbonates and the like.

The coupling step is carried out at a pH from about 4 to about 5, preferably but not necessarily in the presence of an appropriate buffer. The reaction is preferably run in the presence of sodium acetate, which provides a particularly good buffer for such systems. See, for example, Koelsch, *J. Am. Chem. Soc.* 65, 56–58 (1943).

The amount of sodium acetate, or other buffer, used to control the pH of the second step reaction mixture depends upon the amount of hydrochloric acid which still remains after the first step. Sufficient buffer is used to adjust the pH to the desired range.

The amounts of the copper salt and the sulfite are not critical, since they serve merely as catalysts in the reaction. In general, the mixture should contain approximately 5–10 times as much of the copper salt as of the sulfite for best results, and the amount of the salts need be only in the range of 0.01 to 0.10 mole per mole of product to be made.

The simplest way to perform the coupling step is first to mix the water-miscible solvent, the buffer if one is used, the vinyl ester and the two inorganic compounds, and adjust the temperature of the mixture in the desired range. The cool first-step reaction mixture is then added slowly to the vinyl ester mixture. Alternatively, the buffer may be added to the diazonium reaction mixture. It is less convenient but quite possible to add the inorganic compounds to the diazonium mixture, if desired.

The preferred reaction temperature for the coupling step is from about 25° to about 35°, although temperatures from about 0° to about 40° may be used.

The phenethyl ester is the major product of the coupling step, usually being formed in a yield of 60–90 percent. The major by-product of the reaction is the corresponding phenylacetaldehyde, which is usually formed in about 10–30 percent yield. Other by-products are formed in minor amounts. Since the phenylacetaldehyde also forms the desired aminostyrene when reacted with the amine in the third, amination, step of the process, there is no need to purify the second-step product. The minor by-products are readily separated at the end of the process.

Work up of the second-step reaction mixture need be no more complicated than dilution with water and extraction with a solvent to leave water-soluble impurities in the water layer, followed by the neutralization and evaporation of the extraction solvent.

Amination Step

The phenethyl ester may be aminated under any reasonable reaction conditions. A preferred method of amination is to contact the crude product from the second step with the amine in an aqueous medium, which may advantageously be merely water. Organic chemists will recognize that it is most unusual to form an enamine in aqueous medium, since such reactions are usually carried out under anhydrous conditions, with great care being taken to exclude water from the reaction mixture.

However, the amination may also be carried out in any convenient reaction solvent, including aromatics such as benzene and toluene, ethers such as diethyl ether and tetrahydrofuran, and halogenated solvents such as chloroform, carbon tetrachloride and methylene dichloride. Mixtures of solvents, and aqueous solvents such as aqueous alcohols and aqueous ketones may also be used. The temperature of the amination reaction is in the range of from about 0° to about 80°, and the preferred temperature is in the range from about 25° to about 50°.

The amination is carried out in the presence of an acid scavenger, which may conveniently be excess of the amine. Other bases may of course be used, such as inorganic bases including alkali metal hydroxides, carbonates, bicarbonates, acetates, borates and basic phosphates, ammonium hydroxide and carbonate, calcium and magnesium carbonates, oxides, hydroxides and the like, and tertiary amines such as pyridine, triethylamine, triethanolamine and the like. Since the production of each mole of aminostyrene liberates a mole of hydrochloric acid and a mole of acetic acid, two equivalents of the acid scavenger per mole of product are needed.

The reactions in all three steps are relatively rapid, and lengthy reaction times are not necessary. Reaction times vary with the temperature of the reaction, but in general, times in the range of three hours and less are adequate to produce satisfactory yields in each of the three steps.

It will be understood that the present invention may be practiced in a number of different ways, making use of different types or classes of starting compounds, and carrying out the steps of the process in different manners. For example, the following variations of the process are contemplated. Each numbered subparagraph below describes an independent class of starting compounds or an independent process variation; in each class, the variable substituents and the process steps have the general meanings above if not otherwise stated. The process as described above wherein:

1. R represents trifluoromethyl, fluoro, chloro or bromo;
2. R is at the meta position;
3. $R^1$ represents hydrogen;
4. $R^1$ represents fluoro, chloro or bromo;
5. $R^2$ and $R^3$ independently represent $C_1$-$C_3$ alkyl;
6. $R^2$ and $R^3$ independently represent methyl or ethyl;
7. The nitrite is sodium, potassium or lithium nitrite;
8. The nitrite is sodium nitrite;
9. $R^4$ represents $C_1$-$C_3$ alkyl;

10. The water-miscible alcohol or ketone represents a $C_1$-$C_3$ alkanol;

11. The water-miscible alcohol or ketone represents a $C_3$-$C_4$ ketone;

12. The water-miscible alcohol or ketone is methanol or acetone;

13. The copper salt is a sulfate or chloride;

14. The copper salt is cupric sulfate or cupric chloride;

15. The process above wherein a buffer is used in step 2;

16. The process above wherein the buffer is sodium acetate;

17. The process above wherein an aqueous medium is used in step 3;

18. The process above wherein approximately equimolar amounts of the reactants are used;

19. Step 3 of the process, regarded as an entity.

Organic chemists will further recognize that the variations of the invention described in the above subparagraphs may be combined in various manners. Thus, it is contemplated that the various reaction conditions and starting compounds, described in the above subparagraphs, may be combined in any fashion to produce additional manners of practicing the invention. All of these additional manners of practicing the invention, found by combining the above variations of the invention in different combinations and permutations, are species of the invention which are contemplated as preferred embodiments of it.

The following specific examples are given to supplement the above general description.

EXAMPLE 1

β-diethylamino-3-trifluoromethylstyrene

Two l. of concentrated hydrochloric acid and 1 l. of deionized water were combined in a 20-l. flask, and 966 g. of 3-trifluoromethylaniline was added. The mixture was cooled to about $-5°$ and was held in the range $-5°$ to $-10°$ through the following operations.

A solution of 450 g. of sodium nitrite in 1110 ml. of water was added very slowly to the first mixture and the reaction mixture was stirred for one-half hour after the addition. Then, a sodium acetate solution, made by combining 1440 g. of 50 percent sodium hydroxide, 1980 g. of ice and 1098 g. of acetic acid, was added very slowly and the reaction mixture was stirred for one-half hour more after completion of the addition, while nitrogen was slowly bubbled through the reaction mixture.

A 2400 ml. portion of acetic acid, vinyl ester was separately mixed with 3960 ml. of methanol, 150 g. of copper sulfate pentahydrate and 24 g. of sodium sulfite and the mixture was warmed to about 30°. The diazonium reaction mixture prepared in the first step was filtered, while still cold, and was slowly added to the vinyl ester mixture over a period of about 75 minutes, while the temperature was maintained in the range of 33°–35°. Nitrogen was evolved during the addition, and stopped evolving about 5 minutes after the completion of the addition of the diazonium reaction mixture.

When nitrogen stopped evolving, the reaction mixture was poured into 24 l. of room temperature water, and the aqueous mixture was extracted twice with diethyl ether. The combined ether layers were washed first with saturated sodium bicarbonate solution, then twice with water, and then with saturated sodium chloride solution. The organic solution was then dried over anhydrous sodium sulfate and the solvent was removed by evaporation under vacuum. The yield was 1461 g. of oil comprised primarily of 1-chloro-2-(3-trifluoromethylphenyl)ethyl acetate with some 3-trifluoromethylphenyl acetaldehyde.

The crude product was diluted with 7 l. of diethyl ether and the temperature was maintained below 30°. A 1533 g. portion of diethylamine was then added slowly and the reaction mixture was stirred at about 30° for 16 hours. The mixture was then cooled and filtered to remove amine hydrochloride. The solids were washed with additional diethyl ether, the washings were added to the filtrate, and the combined liquids were evaporated under vacuum to produce 1344 g. of β-diethylamino-3-trifluoromethylstyrene, which was identified by nuclear magnetic resonance analysis, showing inflection points at 1.15, 3.18, 5.15, 6.82 and 6.97–7.77 ppm.

EXAMPLE 2

β-diethylamino-3-trifluoromethylstyrene

The process of Example 1 was essentially repeated, on one-sixth scale, except that the sodium acetate solution was added to the vinyl ester-methanol solution, rather than to the diazonium reaction mixture. The yield of the intermediate crude 1-chloro-2-(3-trifluoromethylphenyl)ethyl acetate was 209 g. The amination step proceeded according to Example 1 with similar results.

EXAMPLE 3

β-diethylamino-3-trifluoromethylstyrene

A 161 g. portion of 3-trifluoromethylaniline was added to 300 ml. of concentrated hydrochloric acid, and 170 ml. of water was added to the suspension. The slurry was then cooled to 0° and a solution of 77 g. of sodium nitrite in 180 ml. of water was added dropwise while the temperature was held constant. A suspension of 246 g. of anhydrous sodium acetate in 300 ml. of water was then added to the diazonium reaction mixture, raising its pH to 4.5 to 5.

The mixture above was then added in a small stream to a suspension of 400 ml. of acetic acid, vinyl ester, 25 g. of copper sulfate pentahydrate and 4 g. of sodium sulfite in 600 ml. of methanol, under a nitrogen blanket. After the addition was completed, the temperature of the mixture was allowed to rise to 30°–35° and it was stirred until the evolution of nitrogen stopped, about 30 minutes after completing the addition.

The reaction mixture was diluted with 2 l. of ice water, and was then extracted 3 times with 500 ml. portions of methylene dichloride. The extract was washed 3 times with 500 ml. portions of saturated sodium bicarbonate solution, and twice with 500 ml. portions of water. The extract was then dried over magnesium sulfate and evaporated under vacuum to give 212 g. of oil containing about 80 percent of 1-chloro-2-(3-trifluoromethylphenyl)ethyl acetate.

The oil above was added with stirring to 500 ml. of toluene containing 219 g. of diethylamine. The temperature was not allowed to rise above 45° during the addition. The mixture was allowed to stand for 16 hours, after which 500 ml. of diethyl ether was added and the mixture was filtered. The filtrate was evaporated under vacuum to obtain 350 g. of crude β-diethylamino-3-trifluoromethylstyrene, which was determined to be 86 percent pure by nuclear magnetic resonance analysis.

The NMR spectrum showed inflection points at 1.10, 3.18, 5.10 6.76 and 7.02–7.63 ppm.

EXAMPLE 4

3-chloro-β-dimethylaminostyrene

To 34 ml. of concentrated hydrochloric acid and 17 ml. of water was added 12.7 g. of 3-chloroaniline. The mixture was cooled to −10° with stirring, and to it was added dropwise a solution of 7.5 g. of sodium nitrite in 18.5 ml. of water, while the temperature was held constant between −5° to −10°. After the addition, the mixture was stirred for an additional one-half hour, and to it was then added a sodium acetate solution made of 33 g. of ice, 25 g. of 50 percent sodium hydroxide solution, and 18.3 g. of acetic acid. The mixture was filtered, and the filtrate added while still cold to a mixture of 66 ml. of methanol, 40 ml. of acetic acid, vinyl ester, 2.5 g. of copper sulfate and 0.4 g. of sodium sulfite. During the addition of the diazonium reaction mixture the temperature was held at 32° to 37°.

After the addition was complete and the evolution of nitrogen ceased, the reaction mixture was poured into 400 ml. of water and extracted three times with 200 ml. portions of diethyl ether. The ether extract was washed successively with water, sodium bicarbonate solution, water again and finally with sodium chloride. The washed extract was then dried over magnesium sulfate, filtered and evaporated under vacuum to obtain 15.1 g. of crude 1-chloro-2-(3-chlorophenyl)ethyl acetate.

The phenethyl ester was dissolved in 100 ml. of toluene and to it was added 50 ml. of 25 percent aqueous dimethylamine. The mixture was stirred overnight at room temperature, and was washed with water and dried with magnesium sulfate. Evaporation of the solvent under vacuum yielded an oil which was purified by distillation. The product, 3-chloro-β-dimethylaminostyrene, was obtained in the fractions boiling at 105°–107° at 0.005 mm. in a yield of 5.4 g. Nuclear magnetic resonance analysis determined the product to be 80–85 percent pure. The NMR spectrum showed inflection points at 2.68, 5.0, 6.7 and 6.75–7.38 ppm.

EXAMPLE 5

4-chloro-β-dimethylaminostyrene

The process of Example 4 was followed, starting with 12.7 g. of 4-chloroaniline. Acetone was used instead of methanol in the coupling step. The product was 0.7 g. of 4-chloro-β-dimethylaminostyrene, boiling point 115°–116° at 0.005 mm. The NMR spectrum showed inflection points at 2.75, 5.08, 6.71 and 6.92–7.28 ppm.

EXAMPLE 6

β-dimethylamino-4-fluorostyrene

The process of Example 5 was followed, starting with 11.1 g. of 4-fluoroaniline to obtain 3.8 g. of impure β-dimethylamino-4-fluorostyrene, which was identified by nuclear magnetic resonance analysis, showing inflection points at 2.72, 5.11, 6.63 and 6.55–7.5 ppm.

EXAMPLE 7

3,4-dichloro-β-dimethylaminostyrene

The process of Example 5 was followed, starting with 16.5 g. of 3,4-dichloroaniline to obtain 18.7 g. of impure 3,4-dichloro-β-dimethylaminostyrene, identified by nuclear magnetic resonance analysis. The NMR spectrum showed inflection points at 2.72, 4.93, 6.68 and 6.78–7.45 ppm.

EXAMPLE 8

β-diethylamino-2-nitrostyrene

The first two steps of the process of Example 5 were followed, starting with 13.8 g. of 2-nitroaniline. The yield from the coupling step was 17 g. of crude 1-chloro-2-(2-nitrophenyl)ethyl acetate, which was divided and aminated in two ways.

To 11.8 g. of the crude phenethyl ester in 100 ml. of toluene was added 5.4 g. of diethylamine in 50 ml. of toluene. The mixture was stirred for two hours at room temperature, the toluene was removed under vacuum, and the residue was diluted with diethyl ether. The mixture was filtered and the filtrate was evaporated under vacuum to produce 12.5 g. of crude β-diethylamino-2-nitrostyrene.

Another 6.1 g. portion of the crude ester was dissolved in 50 ml. of diethyl ether and mixed with 2.8 g. of diethylamine dissolved in 20 ml. of diethyl ether. After stirring the amination mixture for 16 hours at room temperature it was filtered and the filtrate was evaporated under vacuum to produce 6.2 g. of crude β-diethylamino-2-nitrostyrene.

The NMR spectrum of the product showed inflection points at 1.17, 3.19, 5.85, 6.87, 6.67–7.5 and 7.73 ppm.

The aminostyrenes of this invention are used as intermediates in a synthesis of a class of 4-pyridones and 4-pyridinethiones which are useful herbicides. The herbicidal compounds are of the formula

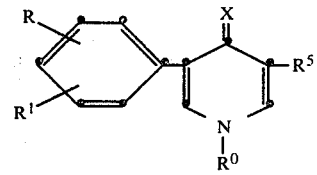

wherein X represents oxygen or sulfur;
R⁰ represents $C_1$–$C_3$ alkyl,
$C_1$–$C_3$ alkyl substituted with halo, cyano, carboxy or methoxycarbonyl,
$C_2$–$C_3$ alkenyl,
$C_2$–$C_3$ alkynyl,
$C_1$–$C_3$ alkoxy,
acetoxy or
dimethylamino,
provided that R⁰ comprises no more than 3 carbon atoms;
R and R¹ are as defined above;
R⁵ represents halo,
hydrogen,
cyano,
$C_1$–$C_3$ alkoxycarbonyl,
$C_1$–$C_6$ alkyl,
$C_1$–$C_6$ alkyl substituted with halo or $C_1$–$C_3$ alkoxy,
$C_2$–$C_6$ alkenyl,
$C_2$–$C_6$ alkenyl substituted with halo or $C_1$–$C_3$ alkoxy,
$C_2$–$C_6$ alkynyl,
$C_3$–$C_6$ cycloalkyl,
$C_3$–$C_6$ cycloalkyl substituted with halo, $C_1$–$C_3$ alkyl or $C_1$–$C_3$ alkoxy,
$C_4$–$C_6$ cycloalkenyl,
$C_4$–$C_8$ cycloalkylalkyl,
phenyl-$C_1$–$C_3$ alkyl, furyl,
naphthyl,
thienyl,
—O—R$^6$,
—S—R$^6$,
—SO—R$^6$,
—SO$_2$—R$^6$ or

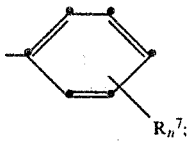

R$^6$ represents C$_1$–C$_3$ alkyl,
C$_1$–C$_3$ alkyl substituted with halo,
C$_2$–C$_3$ alkenyl,
C$_2$–C$_3$ alkenyl substituted with halo,
benzyl,
phenyl or
phenyl substituted with halo, C$_1$–C$_3$ alkyl or C$_1$–C$_3$ alkoxy;
the R$^7$ groups independently represent halo,
C$_1$–C$_8$ alkyl,
C$_1$–C$_8$ alkyl substituted with halo,
C$_1$–C$_8$ alkyl monosubstituted with phenyl, cyano or C$_1$–C$_3$ alkoxy,
C$_2$–C$_8$ alkenyl,
C$_2$–C$_8$ alkenyl substituted with halo,
C$_2$–C$_8$ alkynyl,
C$_2$–C$_8$ alkynyl substituted with halo,
C$_3$–C$_6$ cycloalkyl,
C$_4$–C$_6$ cycloalkenyl,
C$_4$–C$_8$ cycloalkylalkyl,
C$_1$–C$_3$ alkanoyloxy,
C$_1$–C$_3$ alkylsulfonyloxy,
phenyl,
phenyl monosubstituted with halo, C$_1$–C$_3$ alkyl, C$_1$–C$_3$ alkoxy or nitro,
nitro,
cyano,
carboxy,
hydroxy,
C$_1$–C$_3$ alkoxycarbonyl,
—O—R$^8$,
—S—R$^8$,
—SO—R$^8$ or
—SO$_2$—R$^8$;
R$^8$ represents C$_1$–C$_{12}$ alkyl,
C$_1$–C$_{12}$ alkyl substituted with halo,
C$_1$–C$_{12}$ alkyl monosubstituted with phenyl, cyano or C$_1$–C$_3$ alkoxy,
phenyl,
phenyl monosubstituted with halo, C$_1$–C$_3$ alkyl, C$_1$–C$_3$ alkoxy or nitro,
C$_3$–C$_6$ cycloalkyl,
C$_4$–C$_8$ cycloalkylalkyl,
C$_2$–C$_{12}$ alkenyl,
C$_2$–C$_{12}$ alkenyl substituted with halo,
C$_2$–C$_{12}$ alkynyl or
C$_2$–C$_{12}$ alkynyl substituted with halo, provided that R$^8$ comprises no more than 12 carbon atoms;
n represents 0–2; and the acid addition salts thereof.

The pyridones and pyridinethiones are prepared from the aminostyrenes of this invention by a several-step process. Whether the desired product is a pyridone or a pyridinethione, the pyridone is made first and converted to the thione if desired. In the first step, the aminostyrene is reacted with a carbonyl halide to prepare an enaminoketone, as shown below.

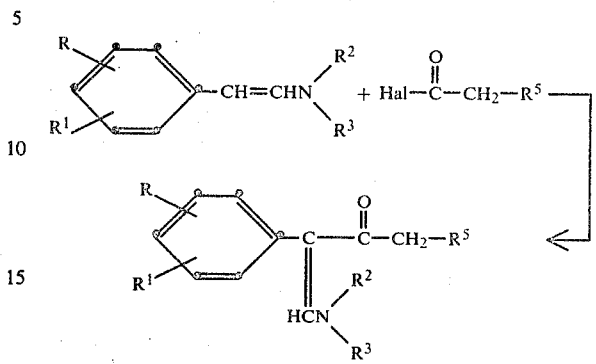

The term Hal in the above formula refers to fluoro, chloro or bromo, of which chloro is preferred.

The enaminoketone is further processed by exchanging with an amine of the formula R$^o$NH$_2$ and by adding either a formyl or an aminoformyl group to the methylene group. The steps may be carried out in either order. When the compound is first formylated or aminoformylated, an intermediate product of one of the formulae below is formed.

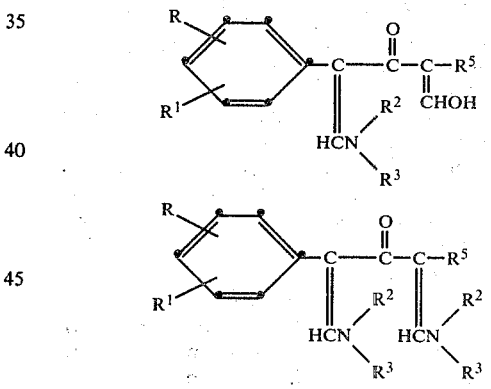

It will be understood that the formyl groups, =CHOH, may advantageously be in the form of the alkali metal salt.

Reaction of either intermediate with an amine, R$^o$NH$_2$, forms the desired pyridone.

When the enaminoketone is first reacted with the amine, R$^o$NH$_2$, the NR$^2$R$^3$ group is replaced with NHR$^o$. Reaction with either a formylating or an aminoformylating agent produces the desired pyridone.

It is also possible, when the 3- and 5-substituents of the herbicidal product are identical, to form the enaminoketone from two molecules of the aminostyrene with phosgene, as shown below.

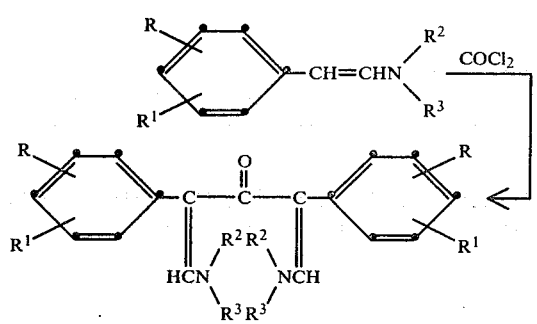

Reaction with the amine, R⁰NH₂, produces the pyridone.

The reactions by which the aminostyrenes are converted to enaminoketones by acylation are performed in the presence of simple bases such as tertiary amines, alkali metal carbonates, magnesium oxide and the like, and in aprotic solvents as described above. Room temperature is preferred but any temperature from about −20° to about 100° may be used.

The formylating agents used in the process are chosen from the common agents used for such reactions. The preferred agents are $C_1$-$C_5$ alkyl esters of formic acid. Similar formylations are discussed in *Organic Synthesis* 300-02 (Collective Vol. III 1955).

The esters are used in the presence of strong bases, of which alkali metal alkoxides are preferred, such as sodium methoxide, potassium ethoxide and lithium propoxide. Other bases may also be used, including alkali metal hydrides, alkali metal amides, and inorganic bases including alkali metal carbonates and hydroxides. Such strong organic bases as diazabicyclononane and diazabicycloundecane are also useful.

Reactions with formylating agents are performed in aprotic solvents such as are regularly used in chemical synthesis. Diethyl ether is usually the preferred solvent. Ethers in general, including solvents such as ethyl propyl ether, ethyl butyl ether, 1,2-dimethoxyethane and tetrahydrofuran, aromatic solvents such as benzene and xylene, and alkanes such as hexane and octane can be used as formylation solvents.

Because of the strong bases used in the formylation reactions, low temperatures produce the best yields. Reaction at temperatures in the range of from about −25° to about 10° is preferred. The reaction mixture may be allowed to warm to room temperature, however, after the reaction has proceeded part way to completion. Reaction times from about 1 to about 24 hours are adequate for economic yields in the formylation reactions.

The aminoformylating agents used in these syntheses may be any compounds capable of reacting with an active methylene group to introduce a =CHNR²R³ group, or its acid addition salt. Such agents are chosen from among s-triazine, the orthoformamides,

HC[NR²R³]₃ the formate ester aminals,

HC[NR²R³]₂ the formamide acetals,

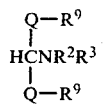

the tris(formylamino)methanes,

and the formiminium halides,

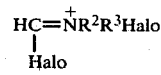

Q in the structures above represents oxygen or sulfur, and $R^9$ represents $C_1$-$C_6$ alkyl or phenyl.

Useful references on the aminoformylating agent include DeWolfe, *Carboxylic Acid Derivatives* 420–506 (Academic Press 1970), and Ulrich, *Chemistry of Imidoyl Halides* 87–96 (Plenum Press 1968). Bredereck et al. have written many papers on such agents and reactions, of which the following are typical. *Ber.* 101, 4048–56 (1968); *Ber.* 104, 2709–26 (1971); *Ber.* 106, 3732–42 (1973); *Ber.* 97, 3397–406 (1964); *Ann.* 762, 62–72 (1972); *Ber.* 97, 3407–17 (1964); *Ber.* 103, 210–21 (1970); *Angew. Chem.* 78, 147 (1966); *Ber.* 98, 2887–96 (1965); *Ber.* 96, 1505–14 (1963); *Ber.* 104, 3475–85 (1971); *Ber.* 101, 41–50 (1968); *Ber.* 106, 3725–31 (1973); and *Angew. Chem Int'l Ed.* 5, 132 (1966). Other notable papers on the subject include Kreutzberger et al., *Arch. der Pharm.* 301, 881–96 (1968), and 302, 362–75 (1969), and Weingarten et al., *J. Org. Chem.* 32, 3293–94 (1967).

Aminoformylations are usually carried out without solvent, at elevated temperatures from about 50° to about 200°. Solvents such as dimethylformamide are sometimes used, however, particularly when it is desirable to raise the boiling point of the reaction mixture.

When aminoformylating with formiminium halides, however, aprotic solvents, such as described above in the description of solvents for formylation, are used at temperatures from about 0° to about 50°, preferably at room temperature. Halogenated solvents such as chloroform and methylene chloride can also be used in such aminoformylations if desired.

The exchange reactions with R⁰NH₂ are best performed in protic solvents of which alkanols are preferred and ethanol is most appropriate. Temperatures from about −20° to about 100° can be used for the exchange reactions. Room temperature is satisfactory and is preferred.

In general, intermediate compounds in the synthesis are not purified, but are simply used in successive steps after separation by extraction, neutralization or removal of excess solvent or reactant as appropriate.

In some instances, as organic chemists will understand, it is necessary to apply additional synthetic steps after the pyridone compound has been formed. For example, it is convenient to form compounds having alkoxy, alkanoyloxy and like $R^7$ substituents by first making the corresponding hydroxy-substituted compound, and then substituting on the oxygen atom.

The pyridinethiones of this invention are readily prepared by the treatment of the corresponding pyridones with $P_2S_5$ in pyridine at reflux temperature, according to known methods.

The 1-acetoxy compounds are made by first making the corresponding 1-hydroxypyridone, using $NH_2OH$ as the amine, and esterifying it with acetic anhydride. The other 1-substituents are provided by appropriate R substituents on the amines, $R^oNH_2$, used to prepare the pyridones.

The synthesis of 4-pyridones from the aminostyrenes of this invention will be exemplified to assure that organic chemists will understand how to use the compounds of the present invention.

EXAMPLE 9

1-methyl-3-phenyl-5-(3-trifluoromethylphenyl)-4(1H)-pyridone

The crude aminostyrene produced in Example 3 was dissolved in 800 ml. of dry pyridine and cooled to 0°-10° while 154 g. of phenylacetyl chloride was slowly added dropwise under a nitrogen blanket. The mixture was stirred for 16 hours while the temperature was allowed to rise to ambient. The mixture was then evaporated under vacuum to a residue which was dissolved in 500 ml. of methylene dichloride and washed, first with three 500 ml. portions of water and then with three 200 ml. portions of saturated sodium bicarbonate solution. The organic solution was then dried over magnesium sulfate, filtered, and evaporated under vacuum at 100° to produce 325 g. of residue which was predominantly 1-diethylamino-4-phenyl-2-(3-trifluoromethylphenyl)-1-buten-3-one.

The residue above was mixed with 300 g. of dimethylformamide dimethyl acetal and was stirred at 100° under nitrogen for 18 hours. Excess acetal was then removed under vacuum and the crude product was added to 200 g. of methylamine hydrochloride in 500 ml. of ethanol and heated at reflux temperature for 16 hours.

The solvent was then removed under vacuum, and the residue was dissolved in 500 ml. of methylene dichloride and washed three times with 250 ml. portions of water. The solvent was evaporated under vacuum and the residue was triturated with 1 l. of 20:1 diethyl ether:acetone. A white precipitate formed, which was separated and dried, and was identified as 96 g. of 1-methyl-3-phenyl-5-(3-trifluoromethylphenyl)-4(1H)-pyridone, m.p. 151°-152°.

|   | Theoretical | Found |
|---|---|---|
| C | 69.30% | 70.95% |
| H | 4.26 | 4.74 |
| N | 4.76 | 4.37 |

EXAMPLE 10

1-methyl-3-phenoxy-5-(3-trifluoromethylphenyl)-4(1H)-pyridone

A 413 g. portion of the aminostyrene prepared in Example 1 was dissolved in 134 g. of pyridine and the solution was cooled to about 0° under a nitrogen cover. To the solution was added 296 g. of phenoxyacetyl chloride in 1 l. of diethyl ether over a 75-minute period. An additional 1 l. of diethyl ether was added and the mixture was stirred for 16 hours at room temperature.

The ether phase was decanted and filtered, and the solids were washed twice with small portions of diethyl ether. The washings were combined with the filtrate and the combined liquids were washed with water, and then with sodium chloride solution. The organic liquid was then dried over sodium sulfate and concentrated to an oil under vacuum. The oil was examined by nuclear magnetic resonance analysis and found to consist mainly of 1-diethylamino-4-phenoxy-2-(3-trifluoromethylphenyl)-1-buten-3-one. The yield was 534 g.

The oil obtained in the step above was dissolved in 2 l. of denatured ethanol and was warmed to about 30°. Eight hundred ml. of 40 percent aqueous methylamine was added to the solution in a small stream, during which addition the temperature of the mixture rose to 37°. The mixture was then stirred for two hours, and was evaporated to an oily residue under vacuum. The residue was dissolved in methylene dichloride, and the solution was washed successively with water, 1 N hydrochloric acid, water and sodium chloride solution. The organic solution was then dried over sodium sulfate and concentrated under vacuum to an oil, which weighed 533 g. and was identified as primarily 1-methylamino-4-phenoxy-2-(3-trifluoromethylphenyl)-1-buten-3-one.

A 284 g. portion of sodium methoxide was mixed with 2 l. of tetrahydrofuran and cooled to 10°. To the methoxide suspension was added the oily residue from the step above dissolved in 1 l. of tetrahydrofuran over a 30-minute period while the temperature was held approximately constant. After the addition, the mixture was stirred at constant temperature for one-half hour more, after which a 370 g. portion of ethyl formate was added over a 20-minute period while the temperature was held at 10-14°. The mixture was stirred for four hours, after which 296 g. of additional ethyl formate was added while the temperature was allowed to rise to 30°. The reaction mixture was stirred for 16 hours at ambient temperature.

A 71 g. portion of sodium methoxide and 74 g. of ethyl formate were then added, and the mixture was stirred for five hours more. The reaction mixture was then concentrated to an oil under vacuum, and the oil was dissolved in methylene dichloride and washed successively with water, dilute hydrochloric acid, water, dilute sodium hydroxide and sodium chloride solution. The organic solution was dried and evaporated under vacuum to produce about 300 g. of oil which was triturated in 3 l. of diisopropyl ether. A precipitate formed which was separated by filtration, washed with additional diisopropyl ether and dried to produce 72 g. of 1-methyl-3-phenoxy-5-(3-trifluoromethylphenyl)-4(1H)pyridone, which showed NMR inflection points at 3.54, 6.82-7.67, 7.83 and 7.97 ppm.

Retreatment of the residual oil with additional sodium methoxide and ethyl formate produced additional product.

I claim:

1. A process for preparing a β-aminostyrene of the formula

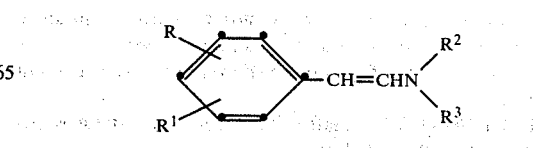

wherein R represents trifluoromethyl, cyano, fluoro, chloro, bromo or nitro;

R$^1$ represents hydrogen, fluoro, chloro, bromo or nitro;

R$^2$ and R$^3$ independently represent C$_1$–C$_3$ alkyl, or R$^2$ and R$^3$ combine with the nitrogen atom to which they are attached to form pyrrolidino, piperidino or morpholino; which process comprises (1) contacting an aniline of the formula

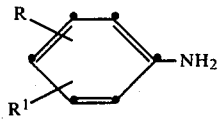

with a nitrite capable of forming diazonium salts, in aqueous hydrochloric acid at a temperature from about −10° to about 10° to form the diazonium chloride salt;

(2) contacting said diazonium salt with a vinyl ester of the formula

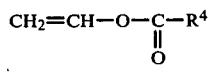

wherein R$^4$ represents C$_1$–C$_3$ alkyl, phenyl, benzyl or hydrogen, in an aqueous, water-miscible alcohol or ketone in the presence of a copper salt and an alkali metal sulfite at a temperature from about 0° to about 40° and a pH from about 4 to about 5 to produce a phenethyl ester of the formula

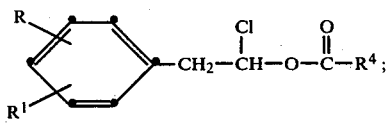

(3) contacting said phenethyl ester with an amine of the formula

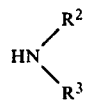

at a temperature from about 0° to about 80° in the presence of an acid scavenger to produce the aminostyrene.

2. The process of claim 1 wherein R represents trifluoromethyl, fluoro, chloro or bromo.

3. The process of claim 1 wherein R$^2$ and R$^3$ independently represent C$_1$–C$_3$ alkyl.

4. The process of claim 1 wherein the nitrite is sodium, potassium or lithium nitrite.

5. The process of claim 1 wherein R$^4$ represents C$_1$–C$_3$ alkyl.

6. The process of claim 1 wherein the copper salt is a sulfate or chloride.

7. The process of claim 1 wherein a buffer is used in step 2.

8. The process of claim 1 wherein approximately equimolar amounts of the reactants are used.

9. The process of claim 1 wherein R is at the meta position.

10. The process of claim 7 wherein the nitrite is sodium, potassium or lithium nitrite.

11. The process of claim 10 wherein R$^4$ represents C$_1$–C$_3$ alkyl.

12. The process of claim 11 wherein the copper salt is a sulfate or chloride.

13. The process of claim 12 wherein R represents trifluoromethyl, fluoro, chloro or bromo.

14. The process of claim 13 wherein R$^2$ and R$^3$ independently represent C$_1$–C$_3$ alkyl.

15. The process of claim 14 wherein approximately equimolar amounts of the reactants are used.

16. The process of claim 15 wherein R is at the meta position.

17. The process of claim 16 wherein R$^1$ represents hydrogen.

18. The process of claim 1 wherein an aqueous medium is used in step 3.

19. The process of claim 18 wherein the copper salt is a sulfate or chloride.

20. The process of claim 19 wherein a buffer is used in step 2.

21. The process of claim 20 wherein approximately equimolar amounts of the reactants are used.

22. The process of claim 21 wherein R$^4$ represents C$_1$–C$_3$ alkyl.

23. The process of claim 22 wherein R$^2$ and R$^3$ independently represent C$_1$–C$_3$ alkyl.

24. The process of claim 23 wherein the nitrite is sodium, potassium or lithium nitrite.

25. The process of claim 24 wherein the water-miscible alcohol or ketone is methanol or acetone.

26. The process of claim 25 wherein R represents trifluoromethyl, fluoro, chloro or bromo.

27. The process of claim 26 wherein R is at the meta position.

28. The process of claim 27 wherein R$^1$ represents hydrogen.

29. A process for preparing a β-aminostyrene of the formula

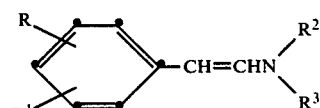

wherein R represents trifluoromethyl, cyano, fluoro, chloro, bromo or nitro;

R$^1$ represents hydrogen, fluoro, chloro, bromo or nitro;

R$^2$ and R$^3$ independently represent C$_1$–C$_3$ alkyl, or R$^2$ and R$^3$ combine with the nitrogen atom to which they are attached to form pyrrolidino, piperidino or morpholino; which process comprises contacting a phenethyl ester of the formula

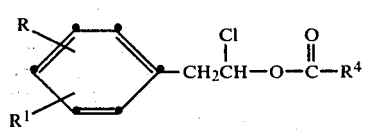

wherein R$^4$ represents C$_1$–C$_3$ alkyl, phenyl, benzyl or hydrogen, with an amine of the formula

at a temperature from about 0° to about 80° in the presence of an acid scavenger to produce the aminostyrene.

30. The process of claim 29 wherein R represents trifluoromethyl, fluoro, chloro or bromo.

31. The process of claim 29 wherein $R^2$ and $R^3$ independently represent $C_1$-$C_3$ alkyl.

32. The process of claim 29 wherein $R^4$ represents $C_1$-$C_3$ alkyl.

33. The process of claim 29 wherein the contacting is in an aqueous medium.

34. The process of claim 29 wherein R is at the meta position.

35. The process of claim 29 wherein $R^1$ represents hydrogen.

36. The process of claim 29 wherein approximately equimolar amounts of the reactants are used.

37. The process of claim 32 wherein $R^2$ and $R^3$ independently represent $C_1$-$C_3$ alkyl.

38. The process of claim 37 wherein R represents trifluoromethyl, fluoro, chloro or bromo.

39. The process of claim 38 wherein the contacting is in an aqueous medium.

40. The process of claim 39 wherein R is at the meta position.

41. The process of claim 40 wherein $R^1$ represents hydrogen.

42. The process of claim 41 wherein approximately equimolar amounts of the reactants are used.

43. The process of claim 33 wherein approximately equimolar amounts of the reactants are used.

44. The process of claim 43 wherein $R^2$ and $R^3$ independently represent $C_1$-$C_3$ alkyl.

45. The process of claim 44 wherein $R^4$ represents $C_1$-$C_3$ alkyl.

46. The process of claim 45 wherein R represents trifluoromethyl, fluoro, chloro or bromo.

47. The process of claim 46 wherein R is at the meta position.

48. The process of claim 47 wherein $R^1$ represents hydrogen.

* * * * *